(12) United States Patent
Hada et al.

(10) Patent No.: US 7,288,175 B2
(45) Date of Patent: Oct. 30, 2007

(54) NOISELESS GAS CONCENTRATION MEASUREMENT APPARATUS

(75) Inventors: Satoshi Hada, Inazawa (JP); Eiichi Kurokawa, Okazaki (JP); Mitsunobu Niwa, Kariya (JP)

(73) Assignee: DENSO Corporation, Kariya, Aichi-pref. (JP)

( * ) Notice: Subject to any disclaimer, the term of this patent is extended or adjusted under 35 U.S.C. 154(b) by 761 days.

(21) Appl. No.: 10/647,215

(22) Filed: Aug. 26, 2003

(65) Prior Publication Data

US 2004/0045824 A1 Mar. 11, 2004

(30) Foreign Application Priority Data

Aug. 30, 2002 (JP) ............... 2002-255578

(51) Int. Cl.
*G01N 27/407* (2006.01)
(52) U.S. Cl. .............. 204/424; 204/425; 204/426; 205/781; 73/23.31
(58) Field of Classification Search ........... 204/424, 204/425, 426; 205/781, 785; 73/23.31
See application file for complete search history.

(56) References Cited

U.S. PATENT DOCUMENTS

| | | | | |
|---|---|---|---|---|
| 4,332,225 A | * | 6/1982 | Cox et al. ............ | 123/697 |
| 5,866,799 A | | 2/1999 | Kato et al. | |
| 6,149,786 A | * | 11/2000 | Patrick et al. ............ | 204/401 |
| 6,336,354 B1 | | 1/2002 | Suzuki et al. | |
| 6,767,449 B2 | | 7/2004 | Cramer et al. | |
| 2002/0050455 A1 | * | 5/2002 | Kurokawa et al. .......... | 204/431 |

FOREIGN PATENT DOCUMENTS

| | | |
|---|---|---|
| JP | 8-313476 | 11/1996 |
| JP | 2885336 | 2/1999 |
| JP | 2000-74873 | 3/2000 |
| JP | 2000-292411 | 10/2000 |
| JP | 2002-372514 | 12/2002 |
| JP | 2003-107041 | 4/2003 |
| JP | 2003-518620 | 6/2003 |

OTHER PUBLICATIONS

Japanese Search Report—Sep. 27, 2005.
Japanese Office Action dated Apr. 17, 2007.

* cited by examiner

*Primary Examiner*—Kaj K. Olsen
(74) *Attorney, Agent, or Firm*—Nixon & Vanderhye P.C.

(57) ABSTRACT

A noiseless circuit structure of a gas concentration measuring apparatus is provided. The gas concentration measuring apparatus includes a control circuit and a gas sensor including a solid electrolyte body, a cell, and a heater serving to heat the solid electrolyte body up to an activation temperature. The control circuit is designed to cancel or remove electric noises arising from an on-off operation of the heater added to a sensor output.

22 Claims, 10 Drawing Sheets

NOISELESS GAS CONCENTRATION MEASUREMENT APPARATUS

BACKGROUND OF THE INVENTION

1. Technical Field of the Invention

The present invention relates generally to a noiseless circuit structure of a gas concentration measuring apparatus equipped with a gas sensor and a heater working to heat a sensor body up to an activation temperature.

2. Background Art

Gas concentration measuring apparatuses for use in automotive internal combustion engines are known in the art which include a gas sensor outputting an electrical signal arising from a given component of gas and a measurement control circuit determining the concentration of the given component using the sensor signal. Such a type of gas concentration measuring apparatus has the gas sensor installed in an exhaust pipe of the internal combustion engine and measure the concentration of oxygen contained in exhaust emissions of the engine for use in control of the engine.

Typical gas sensors use an oxygen ion-conductive solid electrolyte material such as zirconia. For example, gas sensors are known which have a gas chamber into or from which oxygen is allowed to move from or to outside the gas sensor and a cell which is made up of a pair of electrodes affixed to a solid electrolyte body works to pump the oxygen into or out of the gas chamber. Such a type of gas sensor pumps the oxygen into or out of the gas chamber in response to application of voltage to produce a limiting current between the electrodes as a function of concentration of the oxygen. Gas sensors are known which include a plurality of cells of the above type in order to measure the concentration of NOx (nitrogen oxide), CO (carbon monoxide), and HC (hydro carbon).

The gas sensors using the solid electrolyte material need to elevate the temperature of the solid electrolyte material up to an activation temperature thereof. To this end, a heater is typically built in the gas sensor. The power supply to the heater is usually controlled using a PWM signal because of ease and high-precision of adjustment of the power supply. Gas sensors of this type, however, encounter the following drawback.

The heater is, as described above, built in the gas sensor, so that an output of the gas sensor may be sensitive to an electric current flowing through the heater due to its leakage, capacitive coupling, and induction. The inventors of this application have found that the power supply to the heater under the PWM control causes the output of the gas sensor to change sharply due to electric noises produced when the heater is switched between an on-state and an off-state.

SUMMARY OF THE INVENTION

It is therefore a principal object of the present invention to avoid the disadvantages of the prior art.

It is another object of the present invention to provide a noiseless circuit structure of a gas concentration measuring apparatus.

According to one aspect of the invention, there is provided a gas concentration measuring apparatus which may be employed in burning control of an automotive internal combustion engine. The gas concentration measuring apparatus comprises: (a) a gas sensor including a cell and a heater, the cell having a solid electrolyte body and working to produce a sensor signal in the form of an electrical change as a function of concentration of a given component of gas, the heater working to heat the solid electrolyte body; (b) and a measurement control circuit designed to perform a heater power supply control function and an averaging function. The heater power supply control function works to control supply of power to the heater to elevate temperature of the solid electrolyte body up to a desired activation temperature thereof. The averaging function works to average the sensor signal outputted from the gas sensor for a given averaging time range so that a first component of the sensor signal to which a noise arising from a change in the power supplied to the heater is added cancels a second component of the sensor signal to which a noise arising from a change in the power supplied to the heater is added and which is reverse in level to the first component to produce an averaged value. The measurement control circuit determines the concentration of the given component of the gas using the averaged value.

In the preferred mode of the invention, the measurement control circuit controls the supply of power to the heater using a pulse width modulated (PWM) signal so as to place the heater in an on-state and an off-state cyclically. The noise added to the first component of the sensor signal arises from a switch from the off-state to the on-state of the heater. The noise added to the second component of the sensor signal arises from a switch from the on-state to the off-state of the heater.

The averaging time range is identical with a time interval which starts from a leading end of an on-time for which the heater is placed in the on-state and terminates at a trailing end of an off-time for which the heater is placed in the off-state.

The measurement control circuit collects samples of the sensor signal at a given sampling interval and averages the samples over the averaging time range.

The measurement control circuit may calculate a moving average as the averaged value.

The averaging time range may be a natural number multiple of a cycle of the PWM signal.

The cycle of the PWM signal may be a natural number multiple of the sampling cycle of the sensor signal.

The gas concentration measuring apparatus further comprises a high-frequency component removing circuit such as a low-pass filter which works to remove a high-frequency component from the sensor signal outputted from the gas sensor.

The gas sensor includes a first cell and a second cell. The first cell works to pump oxygen contained in the gas admitted into a gas chamber out of the gas chamber or oxygen into the gas chamber from outside the gas chamber to produce a sensor signal in the form of an electrical change as a function of concentration of the oxygen. The second cell works to produce a sensor signal in the form of an electrical change as a function of concentration of a predetermined component of the gas flowing from the gas chamber. The cell may be one of the first and second cells.

The gas sensor may be formed by a lamination of the cell and the heater.

The gas sensor may include a pump cell, a sensor cell, and a monitor cell. The pump cell works to pump oxygen contained in the gas admitted into a gas chamber out of the gas chamber or oxygen into the gas chamber from outside the gas chamber to produce a sensor signal in the form of an electrical change. The sensor cell works to produce a sensor signal in the form of an electrical change as a function of concentration of a predetermined component of the gas flowing from the gas chamber. The monitor cell works to produce a sensor signal in the form of an electrical change as a function of concentration of the oxygen remaining within the gas chamber. The cell may be one of the pump cell, the sensor cell, and the monitor cell. The averaging function also works to average at least one of the sensor signals outputted from the pump cell, the sensor cell, and the monitor cell other than the sensor signal of the cell.

According to the second aspect of the invention, there is provided a gas concentration measuring apparatus which comprises: (a) a gas sensor including a cell and a heater, the cell having a solid electrolyte body and working to produce a sensor signal in the form of an electrical change as a function of concentration of a given component of gas, the heater working to heat the solid electrolyte body up to a desired activation temperature thereof; and (b) a measurement control circuit designed to perform a heater power supply control function. The heater power supply control function works to control supply of power to the heater using a pulse width modulated (PWM) signal so as to place the heater in an on-state and an off-state cyclically. The measurement control circuit samples the sensor signal cyclically and determines the concentration of the given component of the gas using each of sampled values of the sensor signal. When a change in level of one of the sampled values collected in a current sampling cycle from one of the sampled values collected in a previous sampling cycle is greater than a given limit, the sampled value in the current sampling cycle is corrected to a value within a range extending across the sampled value in the previous sampling cycle.

In the preferred mode of the invention, the gas sensor includes a first cell and a second cell. The first cell works to pump oxygen contained in the gas admitted into a gas chamber out of the gas chamber or oxygen into the gas chamber from outside the gas chamber to produce a sensor signal in the form of an electrical change as a function of concentration of the oxygen. The second cell works to produce a sensor signal in the form of an electrical change as a function of concentration of a predetermined component of the gas flowing from the gas chamber. The cell may be one of the first and second cells.

The gas sensor may be formed by a lamination of the cell and the heater.

The gas sensor may include a pump cell, a sensor cell, and a monitor cell. The pump cell works to pump oxygen contained in the gas admitted into a gas chamber out of the gas chamber or oxygen into the gas chamber from outside the gas chamber to produce a sensor signal in the form of an electrical change. The sensor cell works to produce a sensor signal in the form of an electrical change as a function of concentration of a predetermined component of the gas flowing from the gas chamber. The monitor cell works to produce a sensor signal in the form of an electrical change as a function of concentration of the oxygen remaining within the gas chamber. The cell may be one of the pump cell, the sensor cell, and the monitor cell.

When a change in level of one of sampled values of at least one of the sensor signals of the cell outputted from the pump cell, the sensor cell, and the monitor cell which is other than the sensor signal of the cell and collected in a current sampling cycle from one of the sampled values collected in a previous sampling cycle is greater than the given limit, the sampled value in the current sampling cycle is corrected to a value within a range extending across the sampled value in the previous sampling cycle.

According to the third aspect of the invention, there is provided a gas concentration measuring apparatus which comprises: (a) a gas sensor including a cell and a heater, the cell having a solid electrolyte body and working to produce a sensor signal in the form of an electrical change as a function of concentration of a given component of gas, the heater working to heat the solid electrolyte body; and (b) a measurement control circuit designed to perform a heater power supply control function. The heater power supply control function works to control supply of power to the heater using a pulse width modulated (PWM) signal so as to place the heater in an on-state and an off-state cyclically to elevate temperature of the solid electrolyte body up to a desired activation temperature. The measurement control circuit receives an input of the sensor signal and includes a high frequency component removing circuit working to remove a high frequency component from the input of the sensor signal and to produce a high frequency-removed signal. The measurement control circuit determines the concentration of the given component of the gas as a function of the high frequency-removed signal.

Inn the preferred mode of the invention, the gas sensor includes a first cell and a second cell. The first cell works to pump oxygen contained in the gas admitted into a gas chamber out of the gas chamber or oxygen into the gas chamber from outside the gas chamber to produce a sensor signal in the form of an electrical change as a function of concentration of the oxygen. The second cell working to produce a sensor signal in the form of an electrical change as a function of concentration of a predetermined component of the gas flowing from the gas chamber. The cell may be one of the first and second cells.

The gas sensor may be formed by a lamination of the cell and the heater.

The gas sensor may include a pump cell, a sensor cell, and a monitor cell. The pump cell works to pump oxygen contained in the gas admitted into a gas chamber out of the gas chamber or oxygen into the gas chamber from outside the gas chamber to produce a sensor signal in the form of an electrical change. The sensor cell works to produce a sensor signal in the form of an electrical change as a function of concentration of a predetermined component of the gas flowing from the gas chamber. The monitor cell works to produce a sensor signal in the form of an electrical change as a function of concentration of the oxygen remaining within the gas chamber. The cell may be one of the pump cell, the sensor cell, and the monitor cell.

The high frequency component removing circuit also works to remove a high frequency component from the at least one of the sensor signals outputted from the pump cell, the sensor cell, and the monitor cell.

According to the fourth aspect of the invention, there is provided a gas concentration measuring apparatus which comprises: (a) a gas sensor including a cell and a heater, the cell having a solid electrolyte body and working to produce a sensor signal in the form of an electrical change as a function of concentration of a given component of gas, the heater working to heat the solid electrolyte body; and (b) a measurement control circuit designed to perform a heater power supply control function. The heater power supply control function works to control supply of power to the heater using a pulse width modulated (PWM) signal so as to place the heater in an on-state and an off-state cyclically to elevate temperature of the solid electrolyte body up to a desired activation temperature. The measurement control circuit samples the sensor signal cyclically and includes a sample availability determining circuit working to determine whether samples of the sensor signal are available to determination of the concentration of the given component of the gas in terms of an electrical noise or not. The sample availability determining circuit works to determine one of the samples acquired upon a switch between the on-state and the off-state of the heater to be unavailable. The measurement control circuit determines the concentration of the given component of the gas using the samples of the sensor signal from which the one determined to be unavailable is removed.

Inn the preferred mode of the invention, the gas sensor includes a first cell and a second cell. The first cell works to pump oxygen contained in the gas admitted into a gas chamber out of the gas chamber or oxygen into the gas chamber from outside the gas chamber to produce a sensor signal in the form of an electrical change as a function of concentration of the oxygen. The second cell works to produce a sensor signal in the form of an electrical change as a function of concentration of a predetermined component of the gas flowing from the gas chamber. The cell may be one of the first and second cells.

The gas sensor may be formed by a lamination of the cell and the heater.

The gas sensor may include a pump cell, a sensor cell, and a monitor cell. The pump cell works to pump oxygen contained in the gas admitted into a gas chamber out of the gas chamber or oxygen into the gas chamber from outside the gas chamber to produce a sensor signal in the form of an electrical change. The sensor cell works to produce a sensor signal in the form of an electrical change as a function of concentration of a predetermined component of the gas flowing from the gas chamber. The monitor cell works to produce a sensor signal in the form of an electrical change as a function of concentration of the oxygen remaining within the gas chamber. The cell may be one of the pump cell, the sensor cell, and the monitor cell.

The sample availability determining circuit also works to determine whether samples of at least one of the sensor signals outputted from the pump cell, the sensor cell, and the monitor cell other than the sensor signal of the cell are available or not.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
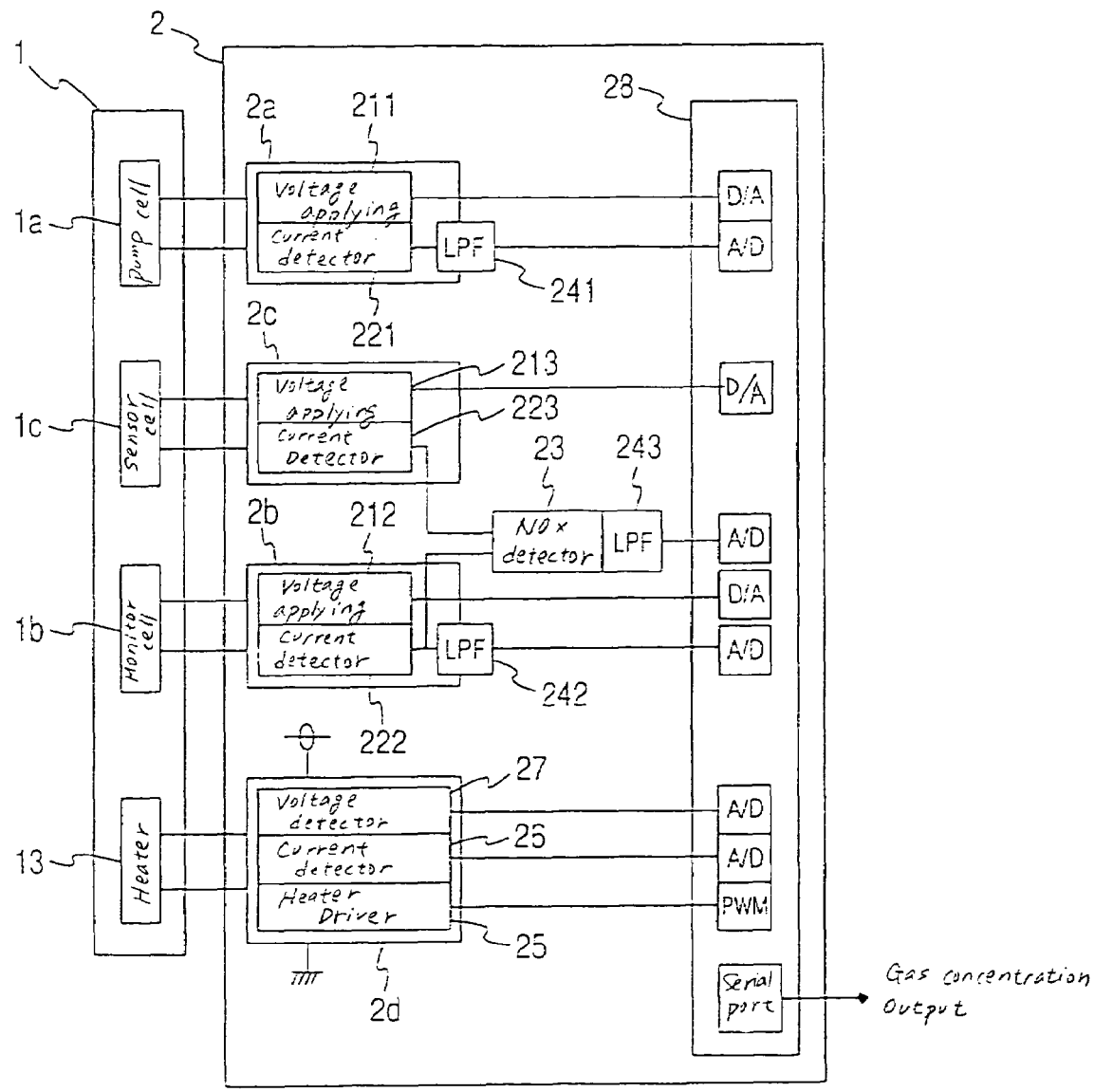
FIG. 1 is a circuit block diagram which shows a gas concentration measuring apparatus according to the invention.

Referring now to the drawings, wherein like numbers refer to like parts in several views, particularly to FIG. 1, there is shown a gas concentration measuring device according to the first embodiment of the invention which consists essentially of a gas sensor 1 and a measurement control circuit 2. The gas sensor 1 is installed, for example, in an exhaust pipe of an automotive internal combustion engine and exposed to exhaust gasses emitted from the engine. The measurement control circuit 2 is installed in a vehicle cabin and coupled with the gas sensor 1 through a wire cable. The measurement control circuit 2 includes a microcomputer 28 which is responsive to outputs from the gas sensor 1 to determine the concentration of oxygen ($O_2$) and nitrogen oxide (NOx) contained in exhaust gasses of the engine.

Figure 2:
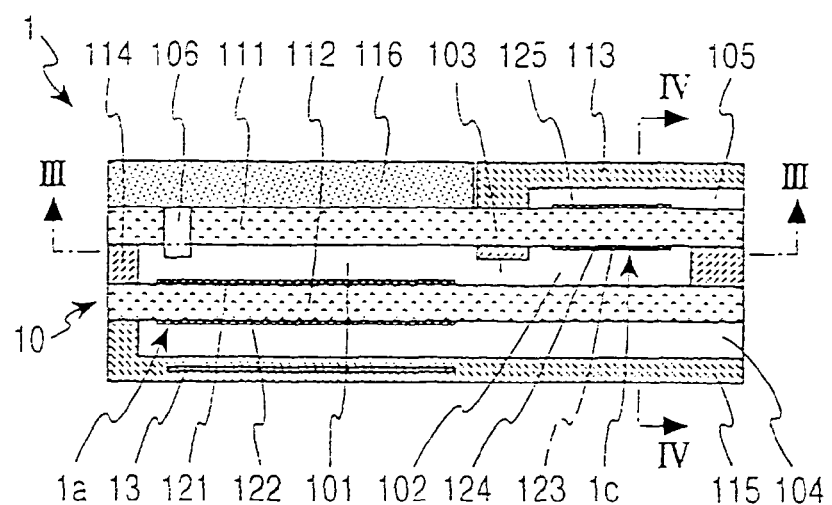
FIG. 2 is a longitudinal sectional view which shows a gas sensor employed in the gas concentration measuring apparatus of FIG. 1.
Figure 3:
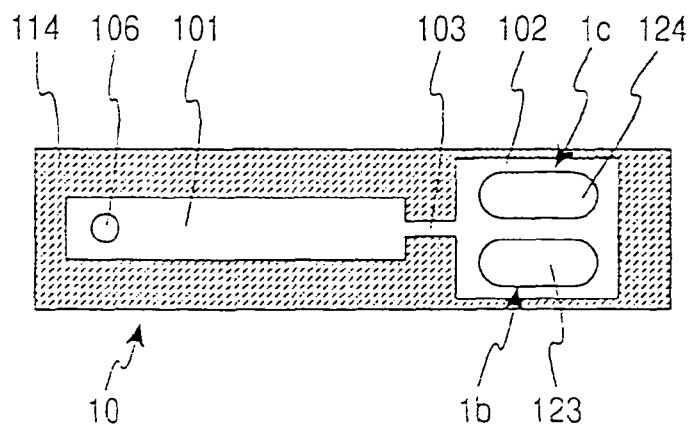
FIG. 3 is a sectional view taken along the line III-III in FIG. 2.
Figure 4:
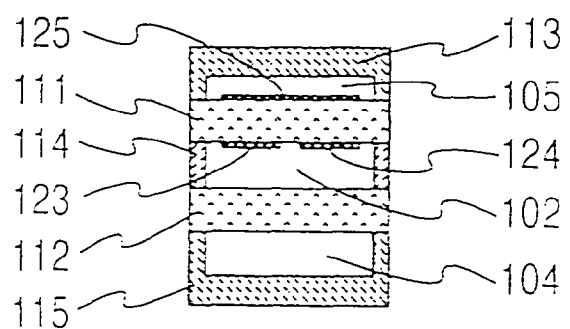
FIG. 4 is a sectional view taken along the line IV-IV in FIG. 2.

The gas sensor 1 is, as clearly shown in FIGS. 2 to 4, formed by a lamination of oxygen ion-conductive solid electrolyte layers 111 and 112 made of zirconia, insulating layers 113 and 114 made of alumina, and a layer 115 made of an insulating material such as alumina or a solid electrolyte material such as zirconia which are laid overlap each other in a thickness-wise direction of the gas sensor 1 in the form of a rectangular plate. The insulating layer 114 interposed between the solid electrolyte layers 111 and 112 has formed therein an opening to define two gas chambers 101 and 102, as will also be referred to as a first and a second chambers below, which communicate with each other through an orifice 103. The first and second chambers 101 and 102 are arrayed in a lengthwise direction of the gas senor 1. The second chamber 102 which is located closer to a base portion (i.e., atmospheric side) of the gas sensor 1 is two times wider than the first chamber 101 which is located closer to a head portion (i.e., gas-sensitive side) of the gas sensor 1.

Air ducts 104 and 105 are formed outside the solid electrolyte layers 111 and 112, respectively. The air ducts 104 and 105 communicate with the atmosphere at the side of the base portion of the gas sensor 1. The first air duct 104 extends over the first chamber 104 through the solid electrolyte layer 112. The second air duct 105 extends over the second chamber 102 through the solid electrolyte layer 111. The installation of the gas sensor 1 in an exhaust system of an automotive engine is achieved by inserting the gas sensor 1 partially into an exhaust pipe through a holder and communicating the air ducts 104 and 105 with the atmosphere.

The solid electrolyte layer 111 has formed therein a pinhole 106 leading to the first chamber 101. A porous diffusion layer 116 is formed on the solid electrolyte layer 111 to avoid intrusion of exhaust fine particles into the firs chamber 101. The pinhole 106 works to admit the gasses to be measured into the first chamber 101 which are flowing outside the porous diffusion layer 116.

The solid electrolyte layer 112 has formed on opposed surfaces thereof electrodes 121 and 122 exposed to the first chamber 101 and the air duct 104, respectively, and defines a pump cell 1a together with the electrodes 121 and 122. The electrode 121 exposed to the first chamber 101 is made of noble metal such as Au—Pt which is inactive with respect to NOx, that is, hardly decomposes NOx.

The solid electrolyte layer 111 has formed on opposed surfaces thereof two pairs of electrodes 125, 123, and 124. The electrode 125 exposed to the air-duct 105 is, as can be seen in FIG. 4, an electrode common to the electrodes 123 and 124. The solid electrolyte layer 111 defines a monitor cell together with the electrodes 123 and 125 and a sensor cell 1c together with the electrode 124 and 125. The electrode 123 of the monitor cell 1b exposed to the second chamber 102 is made of noble metal such as Au—Pt which is inactive with respect to NOx, that is, hardly decomposes NOx. The electrode 124 of the sensor cell 1c exposed to the second chamber 102 is made of noble metal such as Pt which is active with respect to NOx, that is, serves to decompose NOx.

The layer 115 defining the air duct 104 together with the solid electrolyte layer 112 has embedded therein a Pt-made patterned conductor which works as a heater 13 for heating the whole of the gas sensor 1 up to a desired activation temperature. The heater 13 is of an electrical type generating Joule heat.

The exhaust gasses of the engine flowing outside the gas sensor 1, as described above, enters the first chamber 101 through the porous diffusion layer 116 and the pinhole 106. Application of voltage to the pump cell 1a through the electrodes 121 and 122 with the electrode 122 connected to a positive terminal of a voltage source causes oxygen molecules contained in the exhaust gasses to undergo dissociation or ionization, so that the oxygen ($O_2$) is pumped out of the first chamber 101 to the air duct 104. If the concentration of the oxygen ($O_2$) is lower than a desired level in the first chamber 101, a reverse voltage is applied to the pump cell 1a to pump oxygen molecules into the first chamber 101 from the air duct 104 so as to keep the concentration of oxygen ($O_2$) within the first chamber 101 constant. Determination of concentration of oxygen ($O_2$) within the first chamber 101 may be made by setting the applied voltage within a limiting current range and measuring the value of current produced by the pump cell 1a. Since the electrode 121 of the pump cell 1a, as described above, hardly decomposes NOx, NOx gas stays within the first chamber 101.

The exhaust gasses having entered the first chamber 101 diffuse into the second chamber 102. Specifically, the $O_2$ molecules in the exhaust gasses are usually not dissociated by the pump cell 1a completely, so that residual $O_2$ molecules flow into the second chamber 102 and reach the monitor cell 1b and the sensor cell 1c. The application of given voltage to the monitor cell 1b and the sensor cell 1c with the common electrode 125 coupling to the positive terminal of the voltage source causes the gasses within the second chamber 102 to be decomposes so that oxygen ions are discharged to the air duct 105, thereby producing limiting currents in the monitor cell 1b and the sensor cell 1c. Only the electrode 124 of the electrodes 123 and 124 exposed to the second chamber 102 is, as described above, active with NOx, so that the current flowing through the sensor cell 1c will be greater than that flowing through the monitor cell 1b by a value equivalent to the amount of oxygen ion arising from the dissociation or decomposition of NOx on the electrode 124 of the sensor cell 1c. Determination of the concentration of NOx contained in the exhaust gasses is, therefore, achieved by finding a difference between the currents flowing through the monitor cell 1b and the sensor cell 1c. EP0 987 546 A2, assigned to the same assignee as that of this application, teaches control of an operation of this type of gas sensor, disclosure of which is incorporated herein by reference.

Referring back to FIG. 1, the measurement control circuit 2 also includes a pump cell control circuit 2a connected to the pump cell 1a, a sensor cell control circuit 2c connected to the sensor cell 1c, a monitor cell control circuit 2b connected to the monitor cell 1b, and a heater control circuit 2d connected to the heater 13.

The pump cell control circuit 2a, the a sensor cell control circuit 2c, and the monitor cell control circuit 2b have disposed therein voltage applying circuits 211, 213, and 212 which work to apply voltages across the electrodes 121 and 122 of sensor cell 1a, the electrodes 124 and 125 of the sensor cell 1c, and the electrodes 123 and 125 of the monitor cell 1c, respectively. The pump cell control circuit 2a, the a sensor cell control circuit 2c, and the monitor cell control circuit 2b have also disposed therein current detectors 221, 223, and 222 which work to measure currents flowing through the electrodes 121 and 122 of sensor cell 1a, the electrodes 124 and 125 of the sensor cell 1c, and the electrodes 123 and 125 of the monitor cell 1c, respectively. Outputs of the current detector 221 of the pump cell control circuit 2a and the current detector 222 of the monitor cell control circuit 2b are transmitted to the microcomputer 28 through hardware-structured low-pass filters 241 and 242 and sampled by A/D converters to produce a pump cell current and a monitor cell current.

The measurement control circuit 2 also includes a NOx signal detector 23 into which outputs of the current detector 223 of the sensor cell 1c and the current detector 222 of the monitor cell 1b are inputted. The NOx signal detector 23 works to produce a difference between the outputs from the current detectors 223 and 222 which is, in turn, inputted to the microcomputer 28 through a hardware-structured low-pass filter 243 and sampled by the A/D converter to produce a NOx current.

Figure 5:
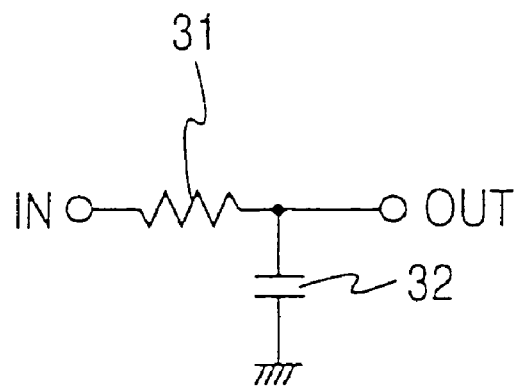
FIG. 5 is a circuit diagram which shows an internal structure of a low-pass filter.

Each of the low-pass filters 241 to 243 is, as clearly shown in FIG. 5, made of an integrating circuit consisting of a resistor 31 and a capacitor 32 which works to remove high-frequency components from an input. Each of the low-pass filters 241 to 343 may alternatively be made of a resistor and an inductance or implemented by an active filer using an operational amplifier. The outputs of the low-pass filters 241 to 243 will also be referred to as sensor signals below.

The heater control circuit 2d includes a heater driver 25, a heater current detector 26, and a heater voltage detector 27. The heater driver 25 is controlled by a PWM (Pulse Width Modulated) signal produced by the microcomputer 28 to control a power supply to the heater 13. The heater current detector 26 works to measure the current flowing through the heater 13 and provides a signal indicative thereof t the microcomputer 28 through an A/D converter. The heater voltage detector 27 works to measure the voltage applied across terminals of the heater 13 and provides a signal indicative thereof to the microcomputer 28 through an A/D converter. The microcomputer 28 uses the outputs of the heater voltage detector 27 and the heater current detector 26 to control the power supply to the heater through the heater driver 25 under feedback control. Specifically, the length of time the heater 13 is supplied with power within a PWM control cycle (i.e., a duty cycle) is increased or decreased as a function of the outputs of the heater current detector 26 and the heater voltage detector 27 to regulate the amount of heat generated by the heater 13.

The measurement control circuit 2 also works to determine impedances of the pump cell 1a, the monitor cell 1b, and the sensor cell 1c. In practice, such a determination is achieved by measuring the impedance between the electrodes 123 and 125 of the monitor cell 1b which will be referred to as sensor impedance ZAC below. The measurement of the sensor impedance ZAC is achieved by shifting a command voltage inputted to the voltage applying circuit 212 either to a positive side or a negative side instantaneously (e.g., for several tens or several hundreds of μsec.) and measuring a resultant change in monitor cell current produced between the electrodes 123 and 125 of the monitor cell 1b through the current detector 222. The change in voltage applied to the monitor cell 1b is blurred by a hardware-structure low-pass filter (not shown) built in the voltage applying circuit 212 and added with a given AC component, thereby avoiding appearance of an excessive peak component at the monitor cell current arising from a capacitor component of the monitor cell 1b in order to improve the accuracy of measuring the sensor impedance ZAC. The microcomputer 28 monitors the change in voltage applied to the monitor cell 1b and the resultant change in monitor cell current to determine the sensor impedance ZAC.

The operation of the gas concentration measuring device of this embodiment will be described blow with reference to FIGS. 6, 7, 8, 9, 10, 11, and 12 which show programs to be executed by the microcomputer 28.

Figure 6:
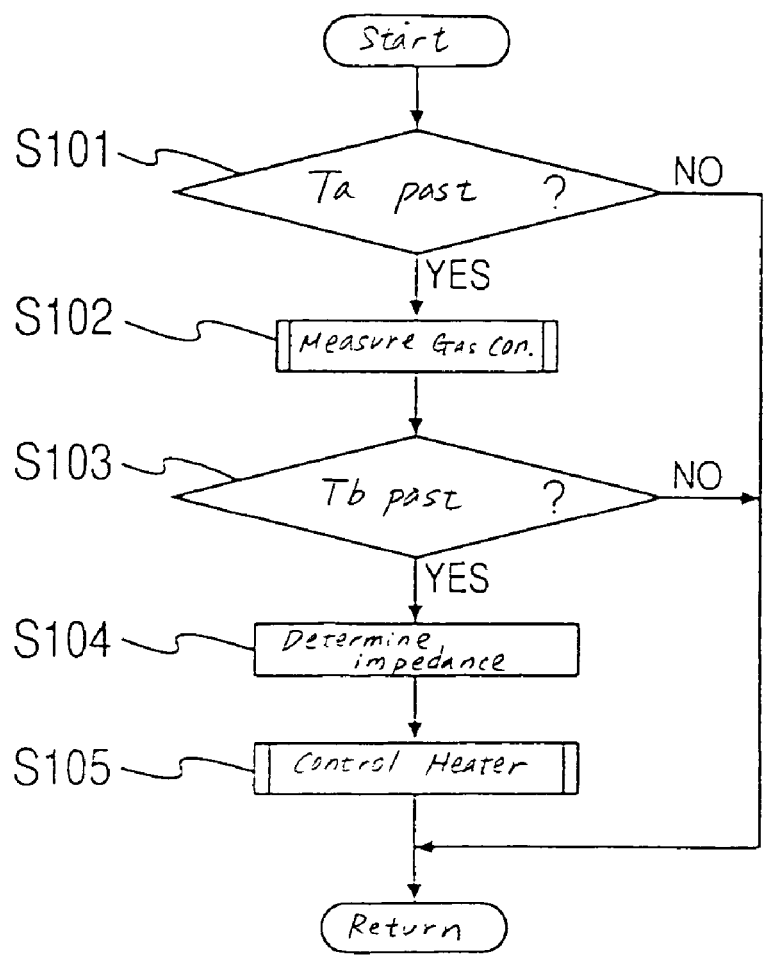
FIG. 6 is a flowchart of a main program performed to determine the concentration of gas and control power supply to a heater.

FIG. 6 shows the maim program performed by the microcomputer 28 upon turning on of the measurement control circuit 2.

After entering the program, the routine proceeds to step 101 wherein it is determined whether a preselected period of time Ta has passed since previous measurement of the concentration of gasses (i.e., $O_2$ and NOx) or not. The preselected period of time Ta corresponds to a measurement cycle of the concentration of gasses and is, for example, 4 ms. If a NO answer is obtained in step 101, then the routine repeats step 101. Alternatively, if a YES answer is obtained, then the routine proceeds to step 102 for measuring the concentration of gasses.

Figure 7:
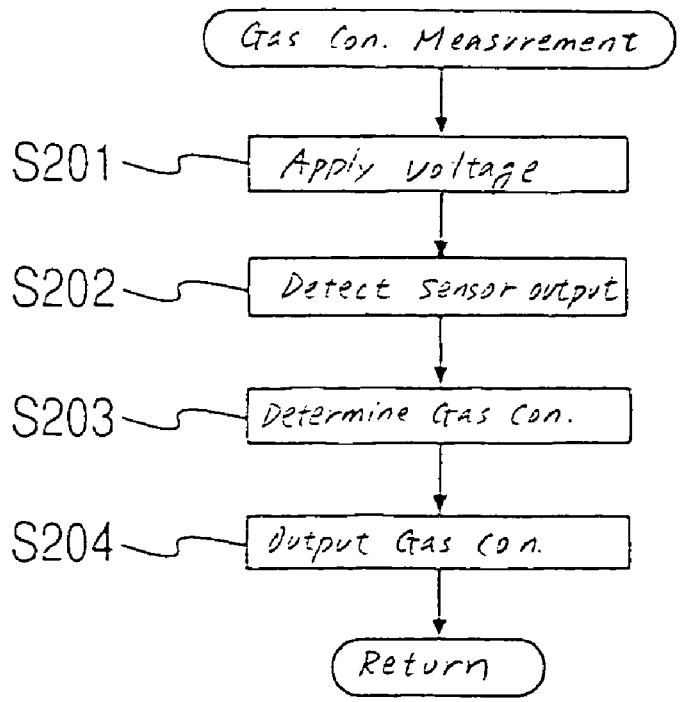
FIG. 7 is a flowchart of a sub-program performed to determine the concentration of gas.

After entering step 102, the routine proceeds to step 201, as shown in FIG. 7, wherein the microcomputer 28 outputs from a D/A converter a command voltage to the voltage applying circuit 211 to apply the voltage to the pump cell 1a as a function of an instant value of the pump cell current. The command voltage is determined by look-up using a map stored in a ROM of the microcomputer 28. The microcomputer 28 also outputs command voltages to the voltage applying circuits 212 and 213 of the monitor cell 1b and the sensor cell 1c to apply voltages to the monitor cell 1b and the sensor cell 1c, respectively. The output of the low-pass filter 242 is used to determine the voltage to be applied to the monitor cell 1b and in another control performed in the microcomputer 28.

The routine proceeds to step 202 wherein outputs of the pump cell 1a, the monitor cell 1b, and the sensor cell 1c, or the sensor signals outputted from the low-pass filters 241 to 243 are, as described above, sampled by the A/D converters. The routine proceeds to step 203 wherein the sensor signals sampled in step 202 are converted into signals indicative of the concentration of oxygen ($O_2$) and NOx in the manner as described below.

In the following steps, the sensor signal outputted from the NOx signal detector 23 through the low-pass filter 243 which is more sensitive to electrical noises in determining the concentration of NOx than that from the pump cell 1a is processed. Of course, the sensor signals outputted from the pump cell 1a and the monitor cell 1b through the low-pass filters 241 and 242 may also be subjected to the same operations.

Figure 8:
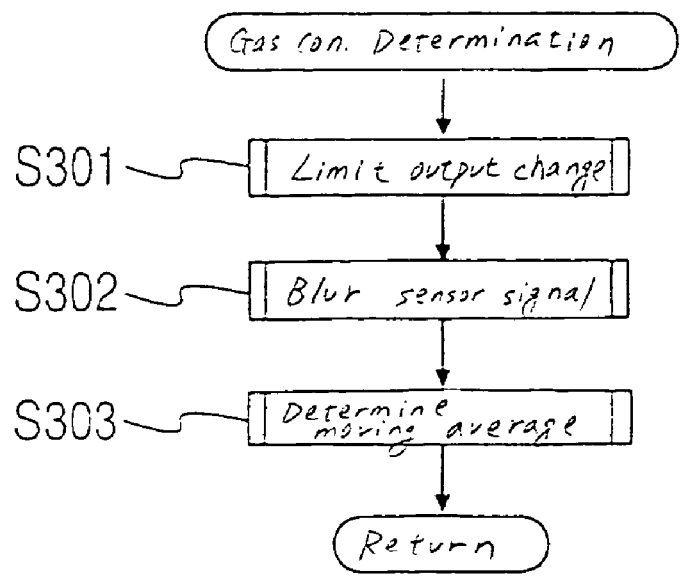
FIG. 8 is a flowchart of a sub-program performed to process a sensor output to reduce or eliminate electric noises added to a sensor output.

Specifically, after entering step 203, the routine proceeds to step 301, as illustrated in FIG. 8, wherein the sensor signals outputted from the monitor cell 1b and the sensor cell 1c sampled in step 202 are each subjected to a change limiting operation as discussed below.

Figure 9:
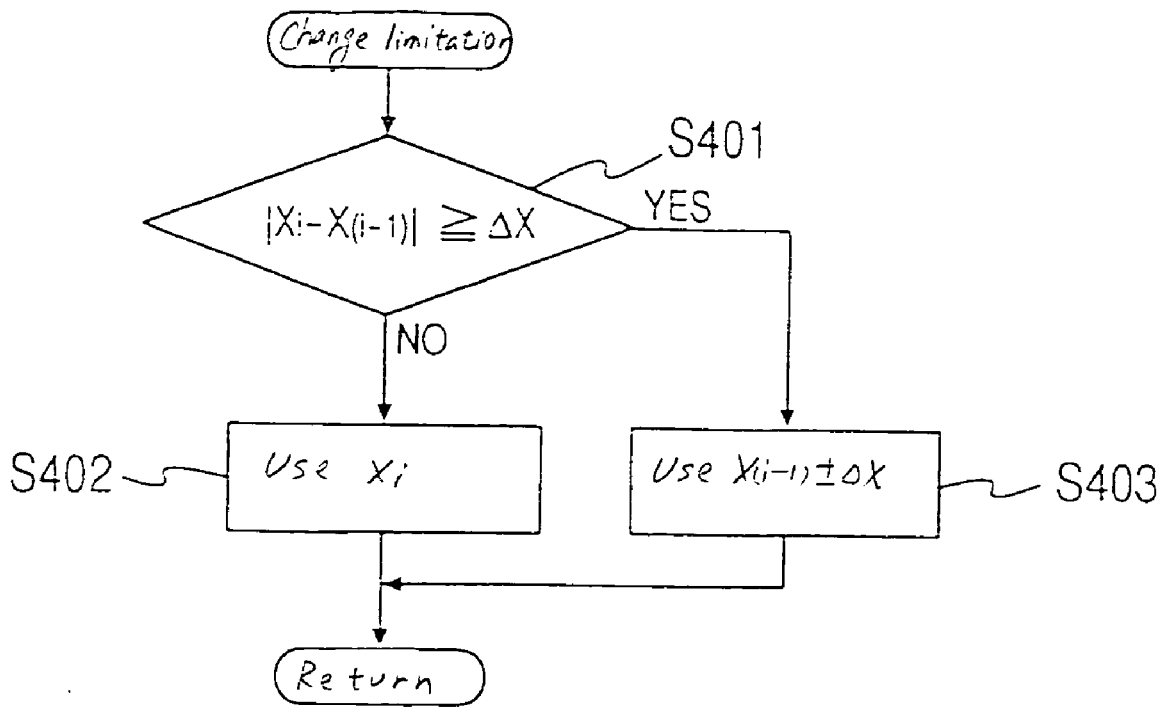
FIG. 9 is a flowchart of a sub-program performed to limit a change in sensor output.

FIG. 9 shows the change limiting operation to be executed in step 301 of FIG. 8. In the following steps, "X" generally indicates the value of the sensor signal, "$X_i$" indicates the value of the sensor signal derived in a current program cycle, and "$X_{i-1}$" indicates the value of the sensor signal derived one program cycle earlier.

First, in step 401, it is determined whether a change in value X of the sensor signal, that is, an absolute value of a difference between the values $X_i$ and $X_{i-1}$ is greater than or equal to a preselected upper change limit $\Delta X$ or not. If a NO answer is obtained (i.e., $|X_i - X_{i-1}| < \Delta X$) is, then the routine proceeds to step 402 wherein the value $X_i$ is determined to be a value of the sensor signal as derived in this program cycle. Alternatively, if a YES answer is obtained (i.e., $|X_i - X_{i-1}| \geq \Delta X$), the routine proceeds to step 403 wherein one of values $X_{i-1} \pm \Delta X$ is determined to be a value of the sensor signal as derived in this program cycle. Specifically, if $X_i \geq X_{i-1}$, meaning that the value $X_i$ in this program cycle has become greater than the value $X_{i-1}$ in the previous program cycle over the upper change limit $\Delta X$, the value $X_{i-1} + \Delta X$ is determined to be the value $X_i$ of the sensor signal as derived in this program cycle. Alternatively, if $X_i \geq X_{i-1}$, meaning that the value $X_i$ in this program cycle has become smaller than the value $X_{i-1}$ in the previous program cycle over the upper change limit $\Delta X$, the value $X_{i-1} - \Delta X$ is determined to be the value $X_i$ of the sensor signal as derived in this program cycle. Specifically, in step 301 of FIG. 8, if a change in the value X of the sensor signal is greater than the upper change limit $\Delta X$, the value X is corrected to be within a range of $\pm \Delta X$.

After step 402 or 403, the routine proceeds to step 302 of FIG. 8 wherein a blur operation is performed.

Figure 10:
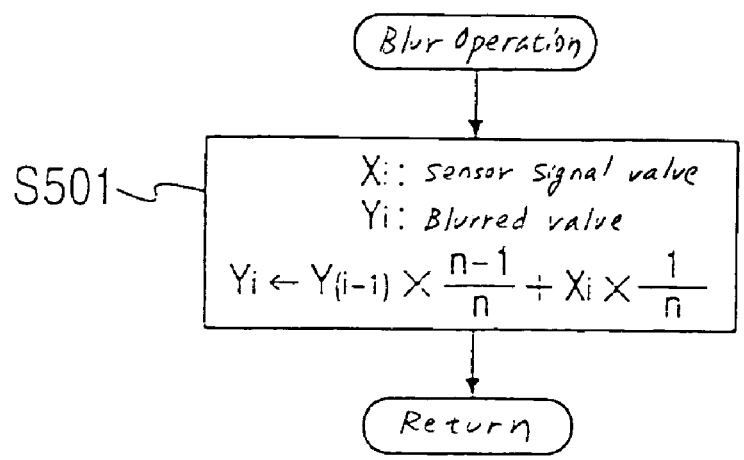
FIG. 10 is a flowchart of a sub-program performed to blur a sensor output.

FIG. 10 shows the blur operation executed in step 302. Specifically, after entering step 302 of FIG. 8, the routine proceeds to step 501 of FIG. 10 wherein a blurred value Y is calculated in the following equation.

$$Y_i = Y_{i-1} \times (n-1)/n + X_i \times 1/n$$

where $Y_i$ indicates a blurred value used in this program cycle, $Y_{i-1}$ indicates a blurred value used one program cycle earlier, and n indicates a natural number which is predetermined experimentally in terms of blurring effects. For instance, n=2 in this embodiment.

After step 501, the routine proceeds to step 303 of FIG. 8 in which a moving average operation is performed.

Figure 11:
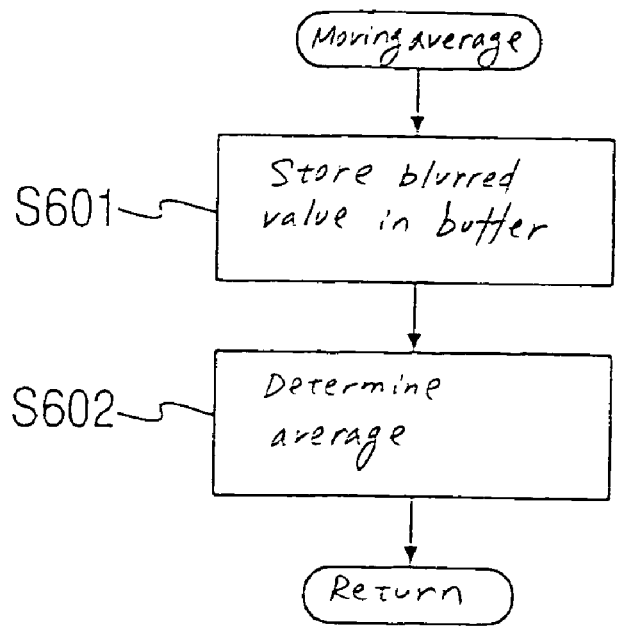
FIG. 11 is a flowchart of a sub-program performed to determine moving averages of a sensor output.

Upon entering step 303, the routine proceeds to step 601 of FIG. 11 wherein the blurred value $Y_i$ is stored in a moving average data buffer. The moving average data buffer works to store a series of blurred values Y derived in sequence over a fixed interval of time (i.e., a predetermined moving average time range) temporarily. When the blurred value $Y_i$ is obtained in this program cycle, the moving average data buffer overwrites an earliest one of the stored blurred values Y with the blurred value $Y_i$ in the same manner as used in a typical method of moving average.

The routine proceeds to step 602 wherein a mean value of the blurred values Y stored in the moving average data buffer is determined to provide a moving average value in this program cycle.

After the above operations on the sensor signal outputted from the NOx signal detector 23 through the low-pass filter 243 is completed, the moving average value is used to determine the concentration of NOx in step 203 of FIG. 7.

The routine proceeds to step 204 wherein a signal indicative of the concentration of NOx as well as a signal indicative of the concentration of $O_2$ determined using the output of the pump cell 1*a* are outputted from a serial port of the microcomputer 28.

After step 204, the routine returns back to the program of FIG. 6 and proceeds to step 103 wherein it is determined whether a preselected period of time Tb has passed or not since the sensor impedance ZAC was measured previously. The preselected period of time Tb corresponds to a measurement cycle of the sensor impedance ZAC and is determined depending upon, for example, operating conditions of the engine. For example, when the engine is in a normal operating condition in which a change in air-fuel ratio is relatively small, Tb=2 sec. When the engine is in a start-up and transient conditions in which the air-fuel ratio changes greatly, Tb=128 msec.

If a YES answer is obtained in step 103, then the routine proceeds to step 104 wherein the sensor impedance ZAC is determined in a manner as described below. The routine proceeds to step 105 wherein a power supply to the heater 13 is controlled. Alternatively, if a NO answer is obtained in step 103, then the routine returns back to step 101. The operations in step 104 and 105 will be discussed in detail below with reference to FIGS. 12 and 13, respectively.

Figure 12:
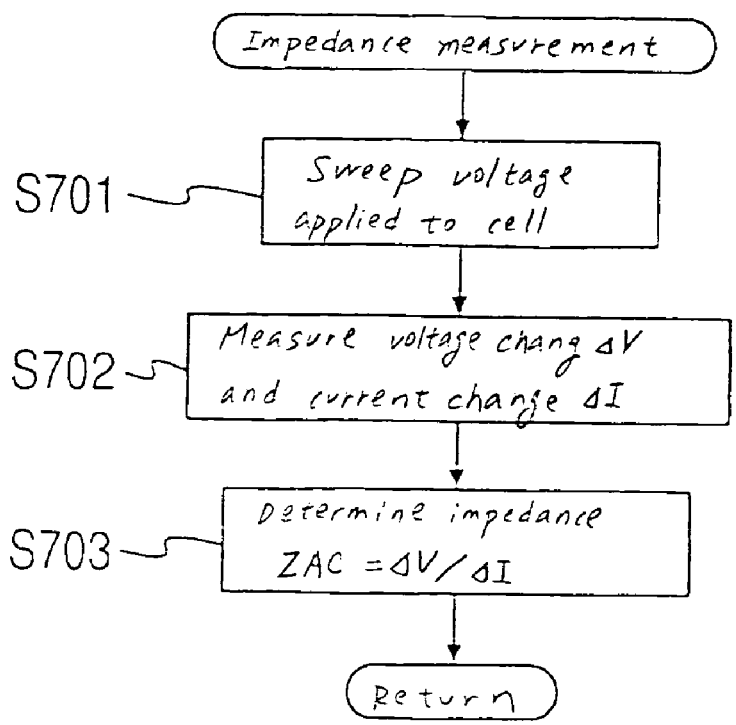
FIG. 12 is a flowchart of a subprogram used to determine the impedance of a gas sensor.

After entering step 104, the routine proceeds to step 701 of FIG. 12 wherein the command voltage outputted to the voltage applying circuit 212 of the monitor cell control circuit 1*b* is shifted in level for a short period of time to change the voltage V applied to the monitor cell 1*b*. The routine proceeds to step 702 wherein a change ΔV in monitor cell-applied voltage V and a resultant change ΔI in monitor cell current are measured. The routine proceeds to step 703 wherein the sensor impedance ZAC is calculated using the voltage change ΔV and the current change ΔI according to the relation of ZAC=ΔV/ΔI. The routine returns back to the program of FIG. 6. The sensor impedance ZAC depends upon the temperature of the solid electrolyte layers 111 and 112 and decreases with a rise in such a temperature. When the temperature of the solid electrolyte layers 111 and 112 rises up to an activation temperature, it will cause oxygen ions to flow through the solid electrolyte layers 111 and 112 easily.

Figure 13:
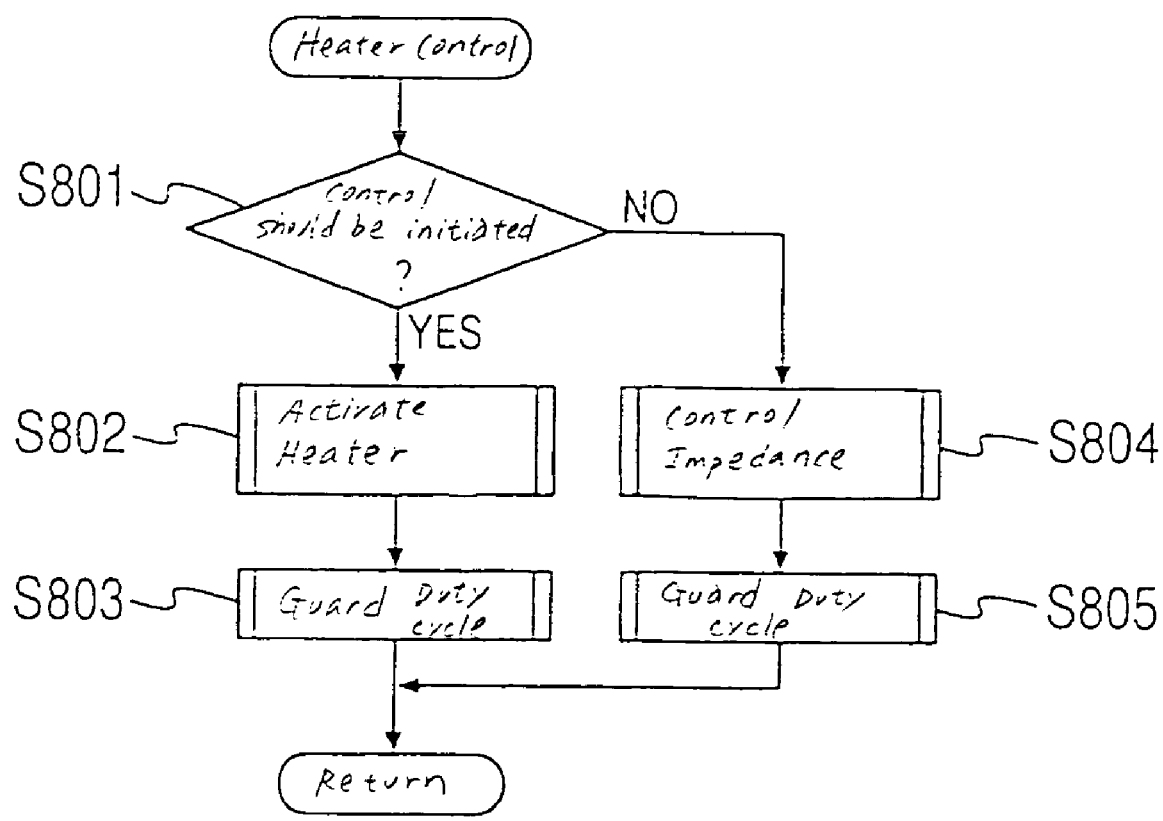
FIG. 13 is a flowchart of a subprogram used to provide a duty cycle-controlled power supply signal to a heater.

The control of power supply to the heater 13 performed in step 105 in FIG. 6 will be described below with reference to FIG. 13.

First, in step 801, it is determined whether a condition in which the control of power supply to the heater 13 should be initiated is met or not. For example, it is determined whether the sensor impedance ZAC is greater than or equal to a given threshold value (e.g., 50 Ω) or not. The threshold value is set slightly greater than a target impedance corresponding to an activation temperature of the solid electrolyte layer. Usually, immediately after start-up of the engine, the temperature of the gas sensor 1 is low, so that the sensor impedance ZAC is high. In this case, it is determined in step 801 that the control of power supply to the heater 13 should be initiated.

If a YES answer is obtained in step 801 meaning that the control of power supply to the heater 13 should be initiated, the routine proceeds to step 802 wherein the PWM signal, which will also be referred to as a heater power supply control signal below, provided to turn on and off a transistor in the heater driver 25 is increased in duty cycle for increasing the temperature of the gas sensor 1 up to a target one corresponding to the above threshold value quickly. The routine proceeds to step 803 wherein the duty cycle of the PWM signal is guarded with a given upper limit. This operation is taught in U.S. Pat. No. 6,870,142 assigned to the same assignee as that of this application, disclosure of which is incorporated herein by reference.

Alternatively, if the temperature of the gas sensor 1 has already risen, a NO answer is obtained in step 801. The routine, thus, proceeds to step 804 wherein the sensor impedance ZAC is controlled under feedback control such as typical PI control. Specifically, a difference between the sensor impedance ZAC and the target impedance is multiplied by a given gain to determine the proportional. The impedance differences accumulated so far is multiplied by a given gain to determine the integral. The duty cycle of the PWM signal is determined using the proportional and integral. The determination of the duty cycle may also be made using techniques as taught in the above U.S. Pat. No. 6,870,142. The routine proceeds to step 805 wherein the duty cycle of the PWM signal is guarded with a given upper limit.

Instead of the sensor impedance ZAC, the admittance that is the reciprocal of the impedance ZAC and a parameter indicating the temperature of the solid electrolyte layers 111 and 112 may be used. Additionally, switching between the impedance ZAC and the admittance may be performed as a function of the temperature of the gas sensor 1 (i.e., the measure of activation of the solid electrolyte layers 111 and 112).

The moving average time range within which the blurred values Y are sampled in sequence and stored in the moving average data buffer stores for determining the moving average in step 303 of FIG. 8 will be described below in detail.

Figure 14:
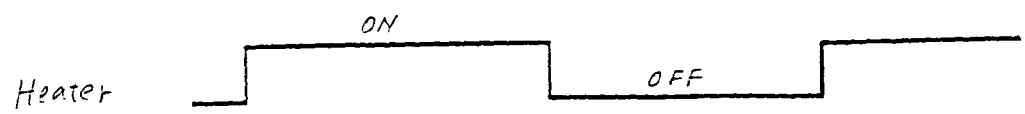
FIG. 14 is a time chart which shows an on-off operation of a heater, a sensor output, a sensor output sampling cycle, an output of a low-pass filter, and a moving average time range.
Figure 14:
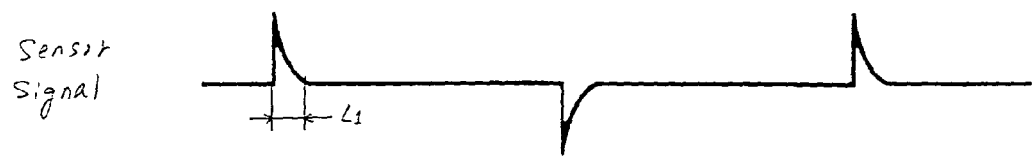
Figure 14:
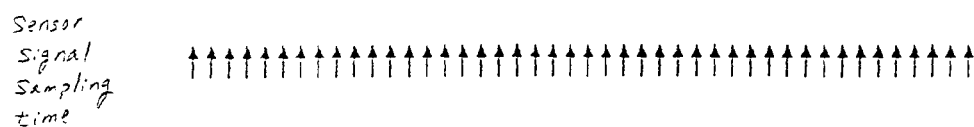
Figure 14:
Figure 14:
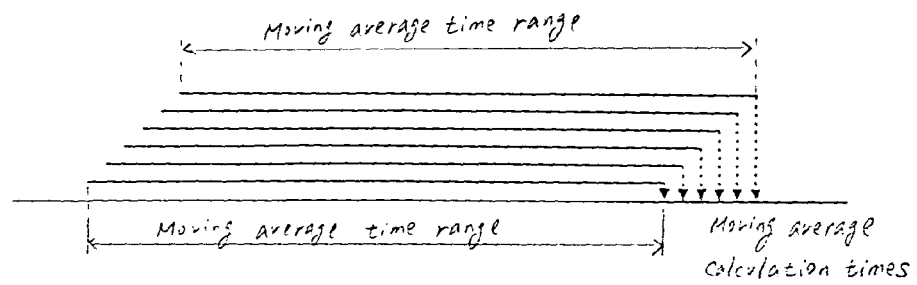

FIG. 14 shows an on-time for which the power is supplied to the heater 13 and an off-time for which the power supply to the heater 13 is cut in a periodic PWM control cycle given by the PWM signal inputted to the heater driver 25, the sensor signal (e.g., the output of the NOx signal detector 23), and sensor signal sampling times at which the sensor signal is sampled by the A/D converter of the microcomputer 28. In the illustrated example, the sensor signal is sampled thirty two (32) times within the PWM control cycle (i.e. an on-to-on time interval of the PWM signal). The moving average data buffer has as many memory locations as the samples of the sensor signal in the PWM control cycle. Specifically, the moving average is determined using the samples of the sensor signal collected in a time interval synchronizing with the PWM control cycle.

Therefore, the 32 blurred values Y stored in the moving average data buffer contain ones sampled at times when the heater 13 is switched from the off-state to the on-state and from the on-state to the off-state. This provides beneficial effects as discussed below.

As compared with this embodiment, a typical moving average operation will be discussed below.

If a moving average of a series of samples of the sensor signal collected over any fixed interval of time is calculated, electrical noises contained in the sensor signal are merely compressed as a function of the interval of time. This is unsuitable for determining the concentration of a trace of gas contained in exhaust emissions of automotive engines such as NOx in terms of electrical noises arising from an on-off operation of the heater 13 using the PWM signal. For instance, the number of samples of the sensor signal to which the noise is added when the heater 13 is switched from the off-state to the on-state may differ from that to which the noises is added when the heater 13 is switched from the on-state to the off-state. The noises produced when the heater 13 is switched from the off-state to the on-state are reverse in level to those produced when the heater 13 is switched from the on-state to the off-state, but however, some of the noises will be left in the sensor signal without being canceled completely in the above case, thus resulting in a decreased accuracy of determining the concentration of NOx.

In this embodiment, the moving average time range coincides with a time duration between a switch from the off-state to the on-state and a subsequent switch from the on-state to the off-state of the heater 13. The noises produced when the heater 13 is switched from the off-state to the on-state are, therefore, cancelled completely by those produced when the heater 13 is switched from the on-state to the off-state, thereby eliminating the noises added to the sensor signal before the concentration of NOx is determined.

The moving average time range is not necessarily identical with the on-to-on time interval of the PWM signal, but may be a natural number multiple of the on-to-on time interval. In other words, the moving average time range is set to the length of time for which the number of samples of the sensor signal collected over a period of time during which the noise arising from the off-to-on switch of the heater 13 will be added to the sensor signal agrees with that collected over a period of time during which the noise arising from the on-to-off switch of the heater 13 will be added to the sensor signal.

The sensor signal from the NOx signal detector 23 is smoothed or blurred by the low-pass filter 243, thereby decreasing a sharp change in the sensor signal arising from addition of the noise immediately after the heater 13 is switched between the on-state and the off-state over a time range $L_2$, as indicated in FIG. 14, which is longer than a time range $L_1$ for which the output of the NOx signal detector 23 is changed greatly by addition of the noise. This provides beneficial effects as discussed below.

If the output of the NOx signal detector 23 before inputted into the low-pass filter 243 is directly sampled by the A/D converter of the microcomputer 28 at an interval greater than the time range $L_1$, it may result in a failure in sampling components of the sensor signal to which the noise is added. However, the noise-caused change in output of the low-pass filter 243 expands over the time range $L_2$ longer than the time range $L_1$, thereby increasing the possibility that the microcomputer 28 fails to sample components of the output of the low-pass filer 243 to which the noise is added.

The change limiting operation, as executed in step 301 of FIG. 8, serves to avoids addition of the noises to the moving average of the sensor signal even if the noises are different in level between a time of the off-to-on switch and a time of the on-to-off switch of the heater 13, thereby improving the accuracy of determining the concentration of NOx further. The change limiting operation also serves to eliminate an adverse effect of suddenly generated noises on the determination of concentration of NOx.

Further, the blur operation, as executed in step 302, also servers to minimizing the effect of the noises added to the sensor signal. Both or either of the blur operation and use of the low-pass filter 243 may be omitted in order to simplify the structure of the measurement control circuit 2. In a case where a period of time during which the noise is added to the sensor signal is too short to sample the noise by the A/D converter, it is advisable that the low-pass filter 243 having an analog structure, as illustrated in FIG. 5, should not be omitted in terms of the accuracy of determining the concentration of NOx. Instead of the blur operation and the use of the low-pass filter 243, the change limiting operation and the moving average operation may be omitted.

The above operations may also be, as described above, performed on the outputs of the pump cell 1a and the monitor cell 1b. The above structural modifications are also useful for the pump cell 1a and the monitor cell 1b.

Figure 15:
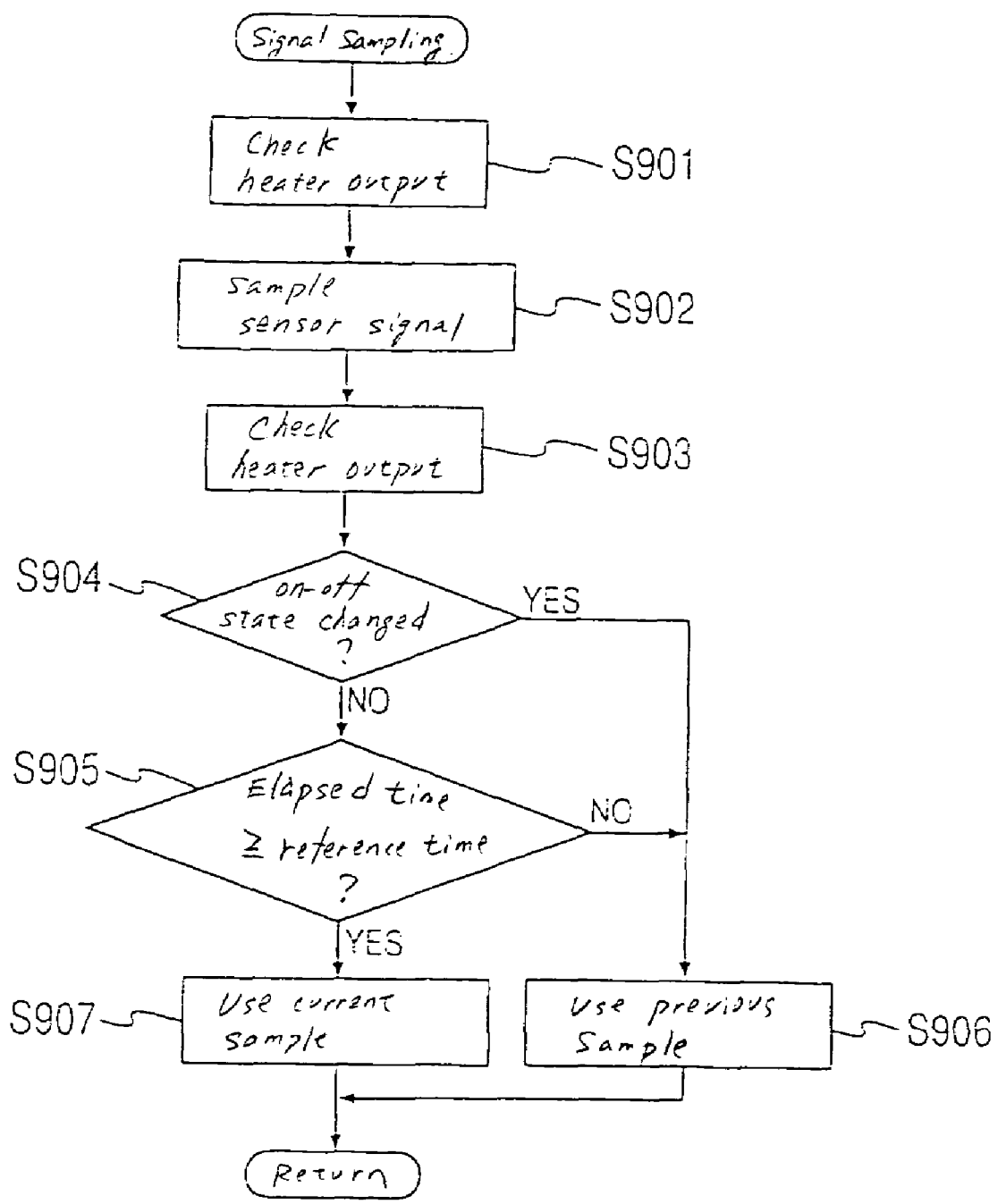
FIG. 15 is a flowchart of an alternative program performed to remove electric noises from a sensor output.

FIG. 15 shows an alternative program to be executed by the microcomputer 28 in the second embodiment of the invention to sample the sensor signal outputted from the low-pass filter 243. The program may also be performed on the sensor signals outputted from the pump cell 1a and the monitor cell 1b.

First, in step 901, the state of the heater 13 is monitored. Specifically, it is determined whether the heater 13 is in the on-state or the off-state using the PWM signal outputted to the heater driver 25. If the heater 13 is determined to be, for example, in the on-state, a heater flag is set to one (1).

The routine proceeds to step 902 wherein the sensor signal is sampled by the A/D converter.

The routine proceeds to step 903 wherein the state of the heater 13 is monitored in the same manner as in step 901. If the heater 13 is determined to be, for example, in the on-state, a heater flag is set to one (1).

The routine proceeds to step 904 wherein it is determined whether the state of the heater 13 has been changed between steps 901 and 903 or not. This determination is achieved by checking the heater flags set in steps 901 and 903. If the state of the heater 13 is determined to have been changed meaning that samples of the sensor signals have been collected in a transition period during which the heater 13 is switched from the on-state to the off-state or vice versa, a YES answer is obtained. A timer is started, as will be described later in detail. Subsequently, the routine proceeds to step 906 wherein samples of the sensor signal collected one program cycle earlier are determined as having been collected in this program cycle.

Alternatively, if a NO answer is obtained in step 904 meaning that the state of the heater 13 has not been changed, the routine proceeds to step 905 wherein it is determined whether a preselected period of time has been elapsed since the latest switch between the on-state and the off-state of the heater 13 or not. This determination is made by checking whether a count value of the timer turned on in step 904 has reached a given reference value or not. The reference value is set greater than or equal to a minimum length of time during which the noise added to the sensor signal immediately after the heater 13 is switched between the on-state and the off-state disappears completely. Thus, if a NO answer is obtained meaning that the noise does not yet disappear completely, then the routine proceeds to step 906 wherein samples of the sensor signal collected one program cycle earlier are determined as having been collected in this program cycle. Alternatively, if a YES answer is obtained meaning that the noise has already disappeared, then the routine proceeds to step 907 wherein samples of the sensor signal collected in this program cycle are to be used in determining the concentration of NOx.

As apparent from the above discussion, the program of FIG. 15 works to replace the samples of the sensor signals to which the noise is added with noiseless ones obtained in a previous program cycle, thereby enabling only the samples of the sensor signal collected after disappearance of the noise following the switch between the on-state and the off-state of the heater 13 to be used in determining the concentration of NOx.

Figure 16:
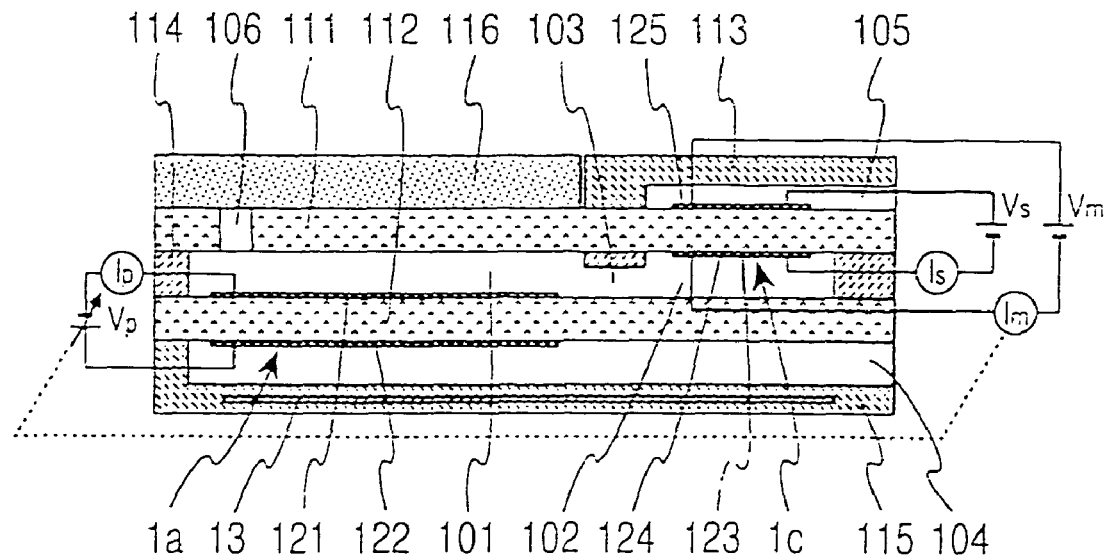
FIG. 16 is a longitudinal sectional view which shows a gas sensor of a type different from the one of FIG. 2 which may be employed in the gas concentration measuring apparatus of FIG. 1.

FIG. 16 shows a modified form of the measurement control circuit 2 in which the monitor current Im produced in the monitor cell 1b is inputted to the microcomputer 28, and the voltage to be applied to the pump cell 1a is so determined under feedback control as to bring that the monitor current Im into agreement with a given reference value.

Figure 17:
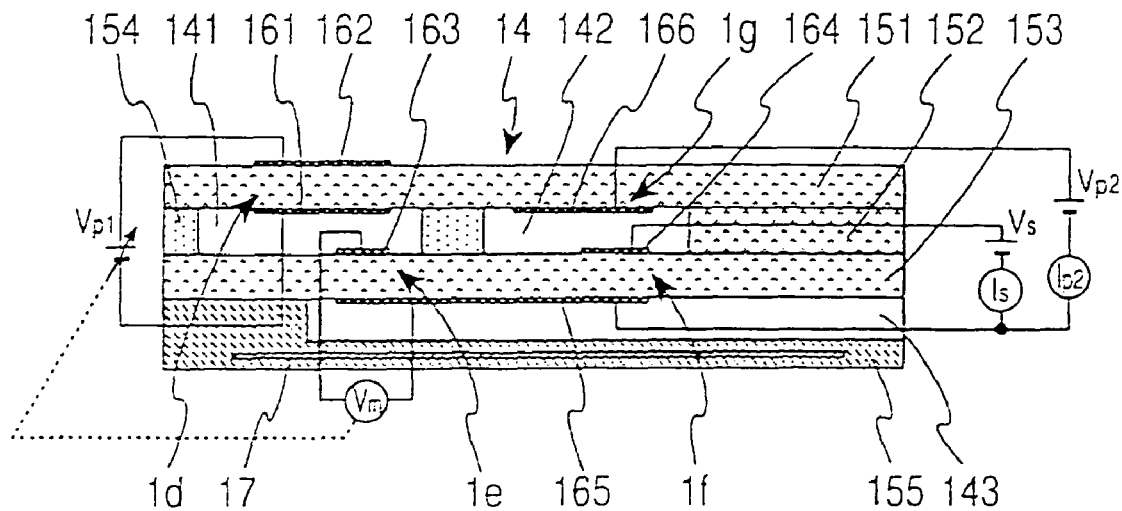
FIG. 17 is a longitudinal sectional view which shows a gas sensor of a type different from the one of FIG. 2 which may be employed in the gas concentration measuring apparatus of FIG. 1.

FIG. 17 shows another type of gas sensor with which the measurement control circuit 2 may be used.

The gas sensor has a base 14 made of a lamination of oxygen ion-conductive solid electrolyte layers 151, 152, and 153 made of zirconia, and a gas-diffusion-rate limiting layer 154 made of insulating material such as porous alumina, and a layer made of insulating material such as alumina and solid electrolyte material.

The solid electrolyte layer 152 and the gas-diffusion-rate limiting layer 154 form a common layer interposed between the solid electrolyte layers 151 and 153. The gas-diffusion-rate limiting layer 154 is located closer to the head portion of the gas sensor, while the solid electrolyte layer 152 is located closer to the base portion of the gas sensor. The solid electrolyte layer 152 and the gas-diffusion-rate limiting layer 154 have formed therein openings to define first and second chambers 141 and 142 arrayed in a lengthwise direction of the gas sensor. The gas-diffusion-rate limiting layer 154 works to admit gasses to be measured into the first chamber 141 and establish gas communication between the first and second chambers 141 and 142.

The layer 155 defines an air duct 143 between itself and the solid electrolyte layer 153. The air duct 143 extends over the first and second chambers 141 and 142 and communicates with the atmosphere. In a case where the gas sensor is installed in an exhaust pipe of an automotive internal combustion engine, the air duct 143 is exposed outside the exhaust pipe.

Electrodes 161 and 162 are affixed to opposed surfaces of the solid electrolyte layer 151 to form a pump cell 1d. The electrode 161 exposed to the chamber 141 is made of a noble metal such as Au—Pt that is inactive with NOx, that is, hardly decomposes NOx.

Electrode 163 and 165 are affixed to opposed surfaces of the solid electrolyte layer 153 to form a monitor cell 1e. The electrode 163 is exposed to the first chamber 141. The electrode 165 is exposed to the air duct 143. The electrode 163 exposed to the first chamber 141 is made of a noble metal such as Au—Pt that is inactive with NOx. The electrode 165 extends up to the second chamber 142 and works as a common electrode shared with a sensor cell 1f and a second pump cell 1g, as will be described below.

An electrode 164 is affixed to a surface of the solid electrolyte layer 153 exposed to the second chamber 142. The electrode 164 forms the sensor cell 1f together with the common electrode 165.

An electrode 166 is affixed to a surface of the solid electrolyte layer 151 exposed to the second chamber 142 to form the second pump cell 1g together with the solid electrolyte layers 151 to 153 and the electrode 165.

The electrode 164 of the sensor cell 1f exposed to the second chamber 142 is made of a noble metal such as Pt that is active with NOx, that is, works to decompose or ionize NOx. The electrode 166 of the second pump cell 1g is made of a noble metal such as Au—Pt that is inactive with NOx.

A patterned conductor is embedded in the layer 155 which works as a heater 17 to heat the whole of the gas sensor up to a desired activation temperature. The heater 17 is of an electrical type generating Joule heat.

The monitor cell 1e produces an electromotive force as a function of the concentration of $O_2$ within the first chamber 141. The measurement control circuit 2 monitors the output of the monitor cell 1e and control the voltage applied to the pump cell 1d to pump oxygen molecules into or out of the first chamber 141 from or to outside the gas sensor so as to bring the output of the monitor cell 1e into agreement with a given reference voltage, that is, to keep the concentration of $O_2$ within the first chamber 141 at a lower level. This also results in a decrease in concentration of $O_2$ within the second chamber 142 down to substantially the same level as that in the first chamber 141.

The oxygen molecules remaining in the second chamber 142 are discharged by the second pump cell 1g outside the gas sensor. The electrode 164 of the sensor cell 1f works to dissociate NOx and produces an electric current as a function of the concentration of NOx within the second chamber 142.

The present invention may be used with another type of gas sensor designed to measure hydro carbon (HC) and/or carbon monoxide (CO) or single-cell gas sensors designed to measure only the concentration of $O_2$. The invention may also be used with gas sensors having a heater not embedded therewithin, unlike the ones shown in FIGS. 2, 16, and 17.

The invention may also be used with gas sensors in which the power supply to the heater is controlled by a pulsed signal other than the PWM signal.

The moving averaging operation, as described above, is performed in a cycle identical with the sampling cycle of the sensor signals, but may alternatively be performed at an interval equivalent to the moving average time range so that time durations during which samples of the sensor signal are averaged may not overlap with each other.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. The gas sensor 1 works to produce the outputs from the pump cell 1a, the sensor cell 1c, and the monitor cell 1b upon application of the voltage thereto, but may alternatively be designed as a known electromotive force generating type which generates an electromotive force from each of the pump cell 1a, the sensor cell 1c, and the monitor cell 1b as a function of the concentration of a corresponding gas component.

What is claimed is:

1. A gas concentration measuring apparatus comprising:
    a gas sensor including a cell and a heater, the cell having a solid electrolyte body and working to produce a sensor signal in the form of an electrical change as a function of concentration of a given component of gas, the heater working to heat the solid electrolyte body; and
    a measurement control circuit designed to perform a heater power supply control function and an averaging function, the heater power supply control function working to control supply of power to the heater to elevate temperature of the solid electrolyte body up to a desired activation temperature thereof, the averaging function working to average the sensor signal outputted from said gas sensor for a given averaging time range so that a first component of the sensor signal to which a noise arising from a change in the power supplied to the heater is added cancels a second component of the sensor signal to which a noise arising from a change in the power supplied to the heater is added and which is reverse in level to the first component to produce an averaged value, said measurement control circuit determining the concentration of the given component of the gas using the averaged value.

2. A gas concentration measuring apparatus as set forth in claim 1, wherein said measurement control circuit controls the supply of power to the heater using a pulse width modulated (PWM) signal so as to place the heater in an on-state and an off-state cyclically, and wherein the noise added to the first component of the sensor signal arises from a switch from the off-state to the on-state of the heater, and the noise added to the second component of the sensor signal arises from a switch from the on-state to the off-state of the heater.

3. A gas concentration measuring apparatus as set forth in claim 2, wherein the averaging time range is identical with a time interval which starts from a leading end of an on-time for which the heater is placed in the on-state and terminates at a trailing end of an off-time for which the heater is placed in the off-state.

4. A gas concentration measuring apparatus as set forth in claim 2, wherein said measurement control circuit collects samples of the sensor signal at a given sampling interval and averages the samples over the averaging time range.

5. A gas concentration measuring apparatus as set forth in claim 4, wherein said measurement control circuit calculates a moving average as the averaged value.

6. A gas concentration measuring apparatus as set forth in claim 5, wherein the averaging time range is a natural number multiple of a cycle of the PWM signal.

7. A gas concentration measuring apparatus as set forth in claim 6, wherein the cycle of the PWM signal is a natural number multiple of the sampling cycle of the sensor signal.

8. A gas concentration measuring apparatus as set forth in claim 1, further comprising a high-frequency component removing circuit which works to remove a high-frequency component from the sensor signal outputted from said gas sensor.

9. A gas concentration measuring apparatus as set forth in claim 1, wherein said gas sensor includes a first cell and a second cell, the first cell working to pump oxygen contained in the gas admitted into a gas chamber out of the gas chamber or oxygen into the gas chamber from outside the gas chamber to produce a sensor signal in the form of an electrical change as a function of concentration of the oxygen, the second cell working to produce a sensor signal in the form of an electrical change as a function of concentration of a predetermined component of the gas flowing from the gas chamber, and wherein said cell is one of the first and second cells.

10. A gas concentration measuring apparatus as set forth in claim 1, wherein said gas sensor is formed by a lamination of the cell and the heater.

11. A gas concentration measuring apparatus as set forth in claim 1, wherein said gas sensor includes a pump cell, a sensor cell, and a monitor cell, the pump cell working to pump oxygen contained in the gas admitted into a gas chamber out of the gas chamber or oxygen into the gas chamber from outside the gas chamber to produce a sensor signal in the form of an electrical change, the sensor cell working to produce a sensor signal in the form of an electrical change as a function of concentration of a predetermined component of the gas flowing from the gas chamber, the monitor cell working to produce a sensor signal in the form of an electrical change as a function of concentration of the oxygen remaining within the gas chamber, and wherein said cell is one of the pump cell, the sensor cell, and the monitor cell.

12. A gas concentration measuring apparatus as set forth in claim 11, wherein the averaging function also works to average at least one of the sensor signals outputted from the pump cell, the sensor cell, and the monitor cell other than the sensor signal of said cell.

13. A gas concentration measuring apparatus comprising:
    a gas sensor including a cell and a heater, the cell having a solid electrolyte body and working to produce a sensor signal in the form of an electrical change as a function of concentration of a given component of gas, the heater working to heat the solid electrolyte body up to a desired activation temperature thereof and
    a measurement control circuit designed to perform a heater power supply control function, the heater power supply control function working to control supply of power to the heater using a pulse width modulated (PWM) signal so as to place the heater in an on-state and an off-state cyclically, said measurement control circuit sampling the sensor signal cyclically and determining concentration of the given component of the gas using each of sampled values of the sensor signal, when a change in level of one of the sampled values collected in a current sampling cycle from one of the sampled values collected in a previous sampling cycle is greater than a given limit, the sampled value in the current sampling cycle being corrected to a value within a range extending across the sampled value in the previous sampling cycle.

14. A gas concentration measuring apparatus as set forth in claim 13, wherein said gas sensor includes a first cell and a second cell, the first cell working to pump oxygen contained in the gas admitted into a gas chamber out of the gas chamber or oxygen into the gas chamber from outside the gas chamber to produce a sensor signal in the form of an electrical change as a function of concentration of the oxygen, the second cell working to produce a sensor signal in the form of an electrical change as a function of concentration of a predetermined component of the gas flowing from the gas chamber, and wherein said cell is one of the first and second cells.

15. A gas concentration measuring apparatus as set forth in claim 13, wherein said gas sensor is formed by a lamination of the cell and the heater.

16. A gas concentration measuring apparatus as set forth in claim 13, wherein said gas sensor includes a pump cell, a sensor cell, and a monitor cell, the pump cell working to pump oxygen contained in the gas admitted into a gas chamber out of the gas chamber or oxygen into the gas chamber from outside the gas chamber to produce a sensor signal in the form of an electrical change, the sensor cell working to produce a sensor signal in the form of an electrical change as a function of concentration of a predetermined component of the gas flowing from the gas chamber, the monitor cell working to produce a sensor signal in the form of an electrical change as a function of concentration of the oxygen remaining within the gas chamber, and wherein said cell is one of the pump cell, the sensor cell, and the monitor cell.

17. A gas concentration measuring apparatus as set forth in claim 16, wherein said measurement control circuit also samples at least one of the sensor signals of the pump cell, the sensor cell, and the monitor cell other than the sensor signal of said cell, when a change in level of one of the sampled values of the at least one of the sensor signals which is collected in a current sampling cycle from one of the sampled values collected in a previous sampling cycle is greater than the given limit, the sampled value in the current sampling cycle being corrected to a value within a range extending across the sampled value in the previous sampling cycle.

18. A gas concentration measuring apparatus comprising:
a gas sensor including a cell and a heater, the cell having a solid electrolyte body and working to produce a sensor signal in the form of an electrical change as a function of concentration of a given component of gas, the heater working to heat the solid electrolyte body; and
a measurement control circuit designed to perform a heater power supply control function, the heater power supply control function working to control supply of power to the heater using a pulse width modulated (PWM) signal so as to place the heater in an on-state and an off-state cyclically to elevate temperature of the solid electrolyte body up to a desired activation temperature, said measurement control circuit sampling the sensor signal cyclically and including a sample availability determining circuit working to determine whether samples of the sensor signal are available to determination of the concentration of the given component of the gas in terms of an electrical noise or not, said sample availability determining circuit working to determine one of the samples acquired upon a switch between the on-state and the off-state of the heater to be unavailable, said measurement control circuit determining the concentration of the given component of the gas using the samples of the sensor signal from which the one determined to be unavailable is removed.

19. A gas concentration measuring apparatus as set forth in claim 18, wherein said gas sensor includes a first cell and a second cell, the first cell working to pump oxygen contained in the gas admitted into a gas chamber out of the gas chamber or oxygen into the gas chamber from outside the gas chamber to produce a sensor signal in the form of an electrical change as a function of concentration of the oxygen, the second cell working to produce a sensor signal in the form of an electrical change as a function of concentration of a predetermined component of the gas flowing from the gas chamber, and wherein said cell is one of the first and second cells.

20. A gas concentration measuring apparatus as set forth in claim 18, wherein said gas sensor is formed by a lamination of the cell and the heater.

21. A gas concentration measuring apparatus as set forth in claim 18, wherein said gas sensor includes a pump cell, a sensor cell, and a monitor cell, the pump cell working to pump oxygen contained in the gas admitted into a gas chamber out of the gas chamber or oxygen into the gas chamber from outside the gas chamber to produce a sensor signal in the form of an electrical change, the sensor cell working to produce a sensor signal in the form of an electrical change as a function of concentration of a predetermined component of the gas flowing from the gas chamber, the monitor cell working to produce a sensor signal in the form of an electrical change as a function of concentration of the oxygen remaining within the gas chamber, and wherein said cell is one of the pump cell, the sensor cell, and the monitor cell.

22. A gas concentration measuring apparatus as set forth in claim 21, wherein the sample availability determining circuit also works to determine whether samples of at least one of the sensor signals outputted from the pump cell, the sensor cell, and the monitor cell other than the sensor signal of said cell are available or not.

* * * * *